United States Patent [19]

Horii et al.

[11] 4,436,918
[45] Mar. 13, 1984

[54] METHOD FOR PRODUCTION OF PEPTIDE, AND ITS INTERMEDIATE

[75] Inventors: Satoshi Horii, Sakai; Hiroshi Fukase, Osaka; Eiji Higashide, Takarazuka, all of Japan

[73] Assignee: Takeda Chemical Industries, Ltd., Osaka, Japan

[21] Appl. No.: 340,337

[22] Filed: Jan. 18, 1982

[30] Foreign Application Priority Data

Jan. 26, 1981 [JP] Japan ............................ 56-10544

[51] Int. Cl.³ ............................................. C07D 207/40
[52] U.S. Cl. ............................ 548/546; 260/112.5 R; 424/177; 548/545; 548/547
[58] Field of Search ............................................. 548/546

[56] References Cited

U.S. PATENT DOCUMENTS 2,666,060  1/1954  Sury et al. ................. 548/546 X
3,224,968  12/1965  Hinkamp ................. 548/546 X

FOREIGN PATENT DOCUMENTS 2058159  2/1971  France ................. 548/546
55-27906  7/1980  Japan .

OTHER PUBLICATIONS

C. A., 89:42977s, (1978), Lulukyan et al.

*Primary Examiner*—Joseph Paul Brust
*Attorney, Agent, or Firm*—Wenderoth, Lind & Ponack

[57] ABSTRACT

The peptide compound represented by the formula:

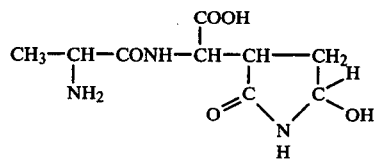

which is useful as a germicide or disinfectant, is produced by reducing a compound of the formula:

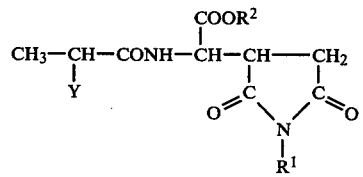

wherein Y is amino group which may optionally be protected; $R^1$ is hydrogen or protective group; and $R^2$ is hydrogen or protective group; and subjecting the reduction product compound to deprotection reaction when required. A compound of the formula:

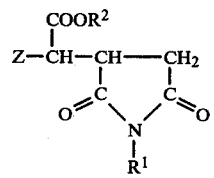

wherein Z is amino group which may optionally be protected; $R^1$ is hydrogen or protective group; and $R^2$ is hydrogen or protective group, is a useful as intermediate for production of the first-mentioned compound.

1 Claim, No Drawings

METHOD FOR PRODUCTION OF PEPTIDE, AND ITS INTERMEDIATE

This invention relates to a method for producing the peptide represented by the formula (I):

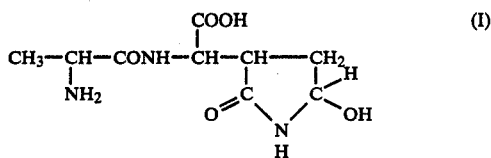

and also to intermediate compounds for the production of said peptide.

The compound of formula (I) i.e. alanyl-2-(5-hydroxy-2-oxopyrrolidin-3-yl)glycine, is a biologically active substance which is active against gram-positive and gram-negative bacteria.

This invention relates to an organic chemical production method for the compound of formula (I), and to intermediate compounds therefor.

Thus, the invention relates to:
(1) a method of producing a compound of the formula (I) which comprises reducing a compound of the formula (II)

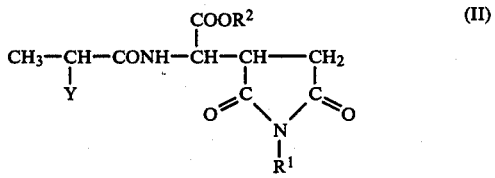

wherein Y is an amino group which may optionally be protected; $R^1$ is hydrogen or a protective group on the N atom of the cyclic imide group; and $R^2$ is hydrogen or a carboxyl-protective group, and subjecting the reduction product to deprotection reaction when required;
(2) compounds of the formula (III)

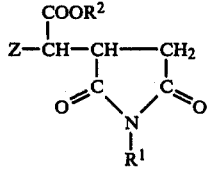

wherein Z is an amino group which may optionally be protected; $R^1$ is hydrogen or a protective group on the N atom of the cyclic imide group; and $R^2$ is hydrogen or a carboxyl-protective group;
(3) compounds of the formula (II)

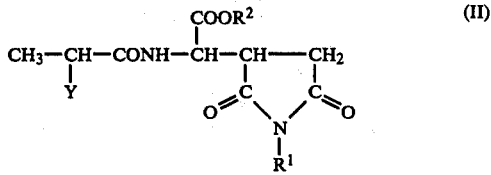

wherein Y is an amino group which may optionally be protected; $R^1$ is hydrogen or a protective group on the N atom of the cyclic imide group; $R^2$ is hydrogen or a carboxyl-protective group.

The compound of formula (I) is produced by reducing a compound of the formula (II) and, if necessary, deprotecting the reduction product. The reducing agent desirable for this purpose is an alkali metal borohydride such as sodium borohydride, potassium borohydride, lithium borohydride, sodium trimethoxyborohydride, etc. This reduction reaction is preferably conducted in an aqueous solution, in a lower alkanol such as methyl alcohol, ethyl alcohol, propyl alcohol, isopropyl alcohol, butyl alcohol, etc., or in a mixture of a lower alkanol and water. The reaction temperature is generally between $-15°$ C. to $50°$ C. and preferably between $0°$ C. and $10°$ C. The pH of the reaction system is generally in the range of 7 to 10 and preferably from 8.5 to 9.5. While the acid that may be used for pH adjustment is virtually optional, such acids as hydrochloric acid, sulfuric acid and phosphoric acid are preferred.

Referring to compounds of the formula (II) and (III), the N-protective group on the cyclic imide group, which is represented by $R^1$, may for example be 2,4-dimethoxybenzyl, to name but a preferred species.

Referring, further, to compounds (II) and (III), a compound in which $R^1$ is 2,4-dimethoxybenzyl can be produced by reacting a compound (II) or (III) in which Y or Z is a protected amino group, $R^2$ is a carboxyl-protecting group and $R^1$ is a hydrogen atom with 2,4-dimethoxybenzyl alcohol in the presence of a phosphine compound and an azodicarboxylic acid diester. As examples of said phosphine compound may be mentioned aromatic and aliphatic tertiary phosphines such as triphenylphosphine, tri-n-butylphosphine, etc., while said azodicarboxylic acid diester may generally be dialkyl or diaralkyl (dimethyl, diethyl, di-n-butyl, dibenzyl, etc.) esters of azodicarboxylic acid. The reaction is generally conducted in a suitable solvent. As examples of said solvent may be mentioned tetrahydrofuran, dichloromethane, chloroform, dichloroethane, dimethylformamide, acetonitrile, ethyl acetate, etc. While this reaction is generally conducted at room temperature, it may be carried out under cooling or heating (e.g. $-20°$ C. to $50°$ C.).

Referring to the case in which the N-protective group on the cyclic imide group, i.e. $R^1$, is 2,4-dimethoxybenzyl, the protective group can be removed by treatment with an acid such as trifluoroacetic acid or hydrogen bromide acetic acid solution generally at room temperature or, if necessary, under cooling or heating (about $-20°$ C. to about $50°$ C.) for generally about 30 minutes to 15 hours.

The carboxyl-protecting group $R^2$ in the compound of formula (II) or (III) may be those carboxyl-protecting groups conventionally utilized in peptide chemistry, such as methyl, ethyl, tert-butyl, 2,2,2-trichloroethyl, benzyl, p-methoxybenzyl, p-nitrobenzyl, trityl, benzhydryl, bis(p-methoxyphenyl)methyl, phenacyl, etc., as well as other carboxyl-protecting groups as described for example by E. Haslam in McOmie's (ed.) "Protective Groups in Organic Chemistry", Plenum Press, N.Y. (1973), Chapter 5 (pp. 183-215), which can be removed without inducing a fission of the pyrrolidine ring.

The carboxyl-protecting group $R^2$ can be eliminated by, among the procedures conventionally used in peptide synthesis, the procedures which do not induce a fission of the pyrrolidine ring. By way of example, benzhydryl, p-methoxybenzyl, etc. can be removed by acid catalyzed cleavage, methyl, ethyl, etc. by alkali catalyzed cleavage, 2,2,2-trichloroethyl by treatment with zinc and acid, and benzyl, p-methoxybenzyl, etc. by catalytic hydrogenolysis.

When Y is a protected amino group, the protective group may be one of the amino-protecting groups conventionally used in peptide chemistry, such as aralkyloxycarbonyl groups, e.g. benzyloxycarbonyl, p-methoxybenzyloxycarbonyl, p-nitrobenzyloxycarbonyl, p-chlorobenzyloxycarbonyl, p-bromobenzyloxycarbonyl, p-methylbenzyloxycarbonyl, etc. and lower alkyloxycarbonyl groups such as tert-butyloxycarbonyl, 2,2,2-trichloroethoxycarbonyl, etc., as well as those other amino-protecting groups which can be eliminated without inducing a fission of the pyrrolidine ring as for example described by J. W. Barton in the above-mentioned literature, "Protective Groups in Organic Chemistry", Plenum Press, New York (1973), Chapter 2 (pp. 43-93).

The amino-protecting group in Y can be eliminated by procedures which are conventionally employed in peptide chemistry for elimination of amino-protecting groups. By way of example, aralkyloxycarbonyl groups such as benzyloxycarbonyl can be removed by catalytic reduction or acid catalyzed cleavage with hydrobromic acid, hydrofluoric acid or the like, 2,2,2-trichloroethoxycarbonyl by treatment with zinc in acetic acid, and tert-butoxycarbonyl by acid catalyzed cleavage with trifluoroacetic acid.

The compound of formula (II) can be produced for example by the following method.

Thus, the compound of formula (II-1)

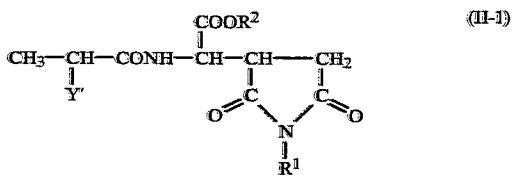

wherein Y' is a protected amino group, R¹ and R² have the same meanings as in the formula (II), can be produced by reacting a compound of the formula (III-1)

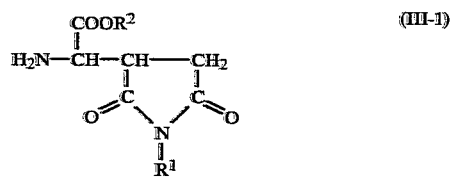

wherein R¹ and R² have the same meanings as defined in the formula (III), with a compound of the formula (IV)

wherein Y' is protected amino, or a reactive derivative of compound (IV).

The protective group in protected amino groups Y' in the formulas (IV) and (II-1) have the same meanings as defined in those of the protected amino groups Y.

The compound of formula (II-1) can be deprotected in the above-described manner to give the compound of formula (II-2).

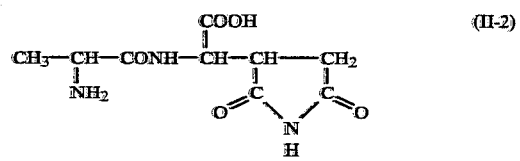

The compound of formula (II-1) and the compound of formula (II-2) fall within the scope of formula (II), and the compound of formula (II-2) can be converted to the compound of formula (I) by reduction of its cyclic imide group.

The reactive derivative of said compound (IV) and the conditions of acylation may be those known in peptide chemistry. As examples of said reactive derivative of compound (IV), there may be mentioned acid anhydrides, activated amides, activated esters, etc. The acid anhydrides include, among others, the acid anhydrides of N-protected alanine with hydrogen halide (e.g. hydrochloric acid, hydrobromic acid), monoalkyl carbonate (e.g. ethyl carbonate, isobutyl carbonate), aliphatic carboxylic acid (e.g. acetic acid, pivalic acid, isovaleric acid), aromatic carboxylic acid (e.g. benzoic acid) and hydrogen azide. The activated amides include, among others, the amides which are prepared by coupling N-protected alanines with imidzole, dimethylimidazole, or 4-dimethylaminopyridinium, etc. The reactive esters include, among others, the p-nitrophenyl ester, 2,4-dinitrophenyl ester, trichlorophenyl ester and pentachlorophenyl ester of alanine with protected amino as well as the N-hydroxysuccinimide ester, N-hydroxyphthalimide ester, etc. of N-protected alanine.

When N-protected alanine itself is used for acylating, the reaction is carried out in the presence of a condensing agent. Examples of such condensing agent are N,N'-dicyclohexylcarbodiimide, N-cyclohexyl-N'-morpholinoethylcarbodiimide, N-cyclohexyl-N'-(4-diethylaminocyclohexyl)carbodiimide, and N-ethyl-N'-(3-dimethylaminopropyl)carbodiimide.

The acylation is generally carried out in a solvent. As the solvent there can be used to advantage water or a mixture of water and such a hydrophilic organic solvent as acetone, methyl ethyl ketone, dioxane, acetonitrile, tetrahydrofuran or dimethylformamide, for instance. The acylation may also be carried out in the presence of a deoxidizer such as an alkali metal hydrogen carbonate, an alkali metal carbonate or such an organic base as trimethylamine, triethylamine, tributylamine, N-methylmorpholine, N-methylpiperidine, N,N-dimethylaniline, pyridine, picoline or lutidine.

The reaction temperature is not critical. In many instances the reaction can be carried out generally at −20° C. to room temperature. If necessary, the reaction can be carried out with heating up to about 50° C.

The compounds of formula (III) in which Z is amino group and R¹ and R² are each hydrogen can be prepared by subjecting a compound of the formula (V)

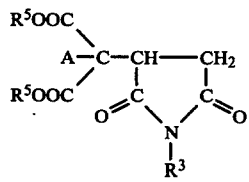

(V)

wherein A is an acylamino group, R³ is hydrogen or a protective group on the N atom of the cyclic imide moiety and R⁵ is a carboxy-protective group, to hydrolysis and decarboxylation, if necessary followed by elimination of said protective group on the N atom of the cyclic imide moiety.

Generally, the hydrolysis and decarboxylation reaction is carried out in a solvent in the presence of an acid. A wide variety of acids commonly used in hydrolysis reactions can be used in the above-mentioned reaction. Such acids include among others inorganic acids such as hydrogen halides (e.g. hydrochloride acid, hydrobromic acid), sulfuric acid and nitric acid, and organic acids such as p-toluenesulfonic acid, trichloroacetic acid and trifluoroacetic acid. Water or a mixture of water and an organic solvent is generally used as the reaction solvent. Preferred examples of the organic solvent to be used in this instance are lower alcohols such as methyl alcohol, ethyl alcohol, propyl alcohol, isopropyl alcohol and butyl alcohol, dioxane, tetrahydrofuran, etc. The reaction is carried out generally at room temperature to 150° C., preferably at 50° C. to the boiling point of the solvent, and the reaction time is generally 1-24 hours.

In the compounds of formula (V), the acyl group of the acylamino moiety represented by A is, for example a straight chain or branched lower alkanoyl group containing 1-4 carbon atoms, such as formyl, acetyl, propionyl, butyryl or isobutyryl, or an aromatic acyl group, such as benzoyl or phthaloyl. The carboxyl-protecting group represented by R⁵ is preferably a straight-chain or branched lower alkyl group containing 1-4 carbon atoms, such as methyl, ethyl, propyl or butyl, for instance. Preferred examples of the acylaminomalonic acid diester are diethyl acetamidomalonate, diethyl formamidomalonate, dimethyl acetamidomalonate, diethyl benzamidomalonate, diethyl phthalimidomalonate, etc.

In the formula (V), and in the formula (VI) and (VII) which appear hereinafter, the protective group R³ on the nitrogen atom of the cyclic imide moiety includes a lower alkyloxycarbonyl group which may optionally be substituted by one or more halogen atoms, namely a lower haloalkyloxycarbonyl group and a lower alkyloxycarbonyl group, the lower alkyl being a straight-chain or branched alkyl containing 1-4 carbon atoms. Examples of the lower haloalkyloxycarbonyl group are mono-, di- or trihalomethoxycarbonyl, mono-, di- or trihaloethoxycarbonyl, mono-, di- or trihalopropoxycarbonyl, mono-, di- or trihalobutoxycarbonyl, etc., including isomers thereof, if any. Said "halo" means fluoro, chloro, bromo or iodo. The alkyloxycarbonyl group includes methoxycarbonyl, ethoxycarbonyl, propoxycarbonyl, butoxycarbonyl, etc., including isomers thereof, if any.

The compounds of formula (V) can be produced, for example, by the method mentioned below.

3-Benzyloxycarbonylamino-2,5-dioxopyrrolidine, synthesized from asparagine or isoasparagine (3-aminosuccinamic acid) by the known method [Journal of the American Chemical Society, vol. 76, page 2467 (1954)], is used as the starting material. The nitrogen atom of cyclic imido group is protected with the above-mentioned protective group R³, and then the benzyloxycarbonyl group, which is the amino protecting group, is eliminated from the benzyloxycarbonylamino group in position 3 so as to give a compound of the formula (VII)

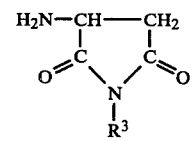

(VII)

wherein R³ has the same meaning as above.

The 3-amino-2,5-dioxopyrrolidine derivative of formula (VII) is then reacted with a nitrosyl halide to give a 3-halo-2,5-dioxopyrrolidine derivative of formula (VI)

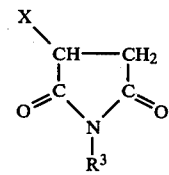

(VI)

wherein X is a bromine or chlorine atom and R³ has the same meaning as above.

The nitrosyl halide can be prepared by reacting nitrogen monoxide with a halogen, preferably by reacting an alkali metal nitrile and an alkali metal halide with an acid. The alkali metal nitrile is, for example, sodium nitrite or potassium nitrite, the alkali metal halide is, for example, potassium iodide, potassium bromide, potassium chloride, sodium bromide or sodium chloride, and the acid is, for example, an inorganic acid such as a hydrogen halide (e.g. hydrochloric acid, hydrobromic acid) or sulfuric acid. Generally, this reaction is carried out in a mixture of water and such an organic solvent as ethyl acetate, methyl acetate, chloroform, dichloromethane, dichloroethane or diethyl ester, generally at a reaction temperature of −20° C. to 50° C., preferably at −10° C. to room temperature.

The compound of formula (VI) is then reacted with an acylaminomalonic acid diester of the formula (VIII)

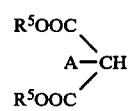

(VIII)

wherein A and R⁵ respectively have the same meaning as in the formula (V), in the presence of a metal base, giving the compound of formula (V).

The compound of formula (V) in which R³ is hydrogen can be prepared by subjecting a compound of the formula (V) in which R³ is a protective group on the N atom of the cyclic imide moiety to a reaction for removing said N-protective group.

When the N-protective group R³ is an optionally halogen-substituted lower alkyloxycarbonyl, for example 2,2,2-trichloroethoxycarbonyl, said protective group can be removed by reaction with zinc in the presence of an organic acid such as formic acid or acetic acid. When the group $R^3$ is methoxycarbonyl or ethoxycarbonyl, said group can be eliminated by treatment with such an alkaline substance as sodium hydroxide, potassium hydroxide or sodium ethylate.

The compound of formula (V) in which $R^3$ is hydrogen can also be prepared by the method mentioned below. Thus, such compound can be prepared by reacting a 2- or 3-halosuccinamic acid ester of the formula (IX)

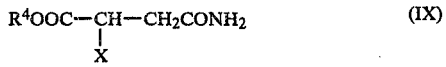

or the formula (IX')

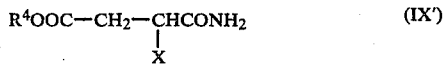

wherein X is halogen and $R^4$ is a carboxyl-protecting group, with an acylaminomalonic acid diester of the formula (VIII) in the presence of a metal base. In this reaction, cyclization for the formation of a 2,5-dioxopyrrolidine ring and the so-called malonic ester synthesis reaction simultaneously take place in one and the same reaction vessel. In this reaction, it is preferable to use at least 2 moles each of the acylaminomalonic acid diester of formula (VIII) and the metal base, per mole of the 2- or 3-halosuccinamic acid ester of formula (IX) or (IX').

The carboxyl-protective group $R^4$ in the 2- or 3-halosuccinamic acid ester (IX) or (IX') is, for example, a straight-chain or branched lower ($C_{1-4}$) alkyl which may optionally be substituted by a halogen atom or halogen atoms, such as methyl, ethyl, 2,2,2-trichloroethyl or tert-butyl, or an aralkyl group such as benzyl, p-methoxybenzyl or p-nitrobenzyl. X means a halogen atom such as fluoro, chloro, bromo or iodo, preferably bromo, iodo or chloro. Preferred examples of the 2- and 3-halosuccinamic acid esters are methyl 2-bromosuccinamate, ethyl 2-bromosuccinamate, methyl 2-chlorosuccinamate, ethyl 2-chlorosuccinamate, methyl 2-iodosuccinamate, ethyl 2-iodosuccinamate, and 3-halosuccinamic acid lower alkyl esters corresponding to the above-mentioned 2-halosuccinamic acid lower alkyl esters. Preferred examples of the metal base are those containing an alkali metal such as sodium, potassium or lithium, generally in the form of an alkali metal alcoholate such as sodium ethylate, lithium ethylate or potassium methylate. Generally, the reaction is carried out in a lower alkanol such as methyl alcohol, ethyl alcohol, propyl alcohol, isopropyl alcohol or butyl alcohol, generally at a temperature of −50° C. to 100° C., preferably at a temperature of −10° C. to room temperature. The reaction time is generally 30 minutes to 5 hours.

The compound (I) of the present invention has antimicrobial activity, as demonstrated by the following test example:

| Antibacterial activity of D-alanyl-2-(5-hydroxy-2-oxopyrrolidin-3-yl)glycine | |
|---|---|
| Test organism | MIC (μg/ml) |
| Bacillus subtilis PCI 219 | 6–24 |

-continued

| Antibacterial activity of D-alanyl-2-(5-hydroxy-2-oxopyrrolidin-3-yl)glycine | |
|---|---|
| Test organism | MIC (μg/ml) |
| Escherichia coli NIHJ JC-2 | 3–12 |
| Proteus vulgaris IFO 3045 | 0.6–2.4 |
| Proteus morganii IFO 3168 | 3–12 |
| Proteus vulgaris IFO 3988 | 1.6–4.8 |

The above-mentioned minimum inhibitory concentration (MIC; μg/ml) values were determined by the agar dilution method using the medium mentioned below. The inoculum size was one loopful with a viable count of $10^6$ CFU/ml. Incubation was performed at 37° C. for 18–20 hours.

Medium: glucose 3%, sodium glutamate 0.5%, $K_2HPO_4$ 0.05%,
$MgSO_4.7H_2O$ 0.05%, KCl 0.05%, yeast extract (Difco) 0.05%,
Casamino acid 0.02%, agar 1.5% (pH 7.0).

This substance can be used as a disinfectant. Thus, for example, its aqueous solution having a concentration of about 10–100 μg/ml can be used for disinfecting bird cages, laboratory appliances and human hands, for instance.

The following reference examples and examples will illustrate the invention in more detail.

REFERENCE EXAMPLE 1

3-Benzyloxycarbonylamino-1-(2,2,2-trichloroethoxycarbonyl)succinimide

In 50 ml of dimethylformamide was dissolved 25.0 g of 3-benzyloxycarbonylaminosuccinimide and the solution was cooled to −40° to −45° C. To the solution was added 15.4 ml of triethylamine, followed by dropwise addition of 25 g of 2,2,2-trichloroethoxycarbonyl chloride under stirring at the same temperature as above. The mixture was further stirred at 0°–3° C. for one hour and poured into an ice-cooled mixture of 600 ml of ethyl acetate and 200 ml of 10% phosphoric acid. After the mixture was stirred, the ethyl acetate layer was separated and the aqueous layer was further extracted with ethyl acetate. These ethyl acetate extracts were combined, washed with water, dried over magnesium sulfate and concentrated under reduced pressure. To the residue was added ethyl ether and the mixture was allowed to stand in a refrigerator to give the 2,2,2-trichloroethoxycarbonyl derivative as crystals. Yield 22 g.

Elemental analysis: Calcd. for $C_{15}H_{13}N_2O_6Cl_3$: C, 42.52; H, 3.09; N, 6.61; Cl, 25.11. Found: C, 42.43; H, 3.01; N, 6.68; Cl, 25.09.

IR $\nu_{max}^{KBr}$ cm$^{-1}$: 1830, 1780, 1717, 1700.

NMR(DMSO-$d_6$)δ: 7.49(1H,d,J=8,—CON$\underline{H}$—), 7.30(5H,s,$C_6H_5$—), 5.07(2H,s,—O—C$\underline{H_2}$—), 4.95(2H,s,—OC$\underline{H_2}$—), 4.4–4.75(1H,m,3-$\underline{H}$), 3.12(1H,dd,J=9.5 & 18, 4-$\underline{H}$), 2.81(1H,dd,J=7 & 18,4-$\underline{H}$).

REFERENCE EXAMPLE 2

1-Ethoxycarbonyl-3-benzyloxycarbonylaminosuccinimide

In the same manner as Reference Example 1, 25.0 g of 3-benzyloxycarbonylaminosuccinimide was reacted with 13.0 g of ethoxycarbonyl chloride. The procedure gave 18.7 g of the 1-ethoxycarbonyl derivative as crystals.

Elemental analysis: Calcd. for $C_{15}H_{16}N_2O_6$: C, 56.25; H, 5.04; N, 8.75. Found: C, 56.42; H, 5.07; N, 8.78.

IR $\nu_{max}^{KBr}$ cm$^{-1}$: 1820, 1760, 1730, 1720

NMR(CDCl$_3$)δ: 7.28(5H,s,C$_6$H$_5$—), 6.00(1H,d,J=8,—CON$\underline{H}$—), 5.04(2H,s,C$_6$H$_5$—C$\underline{H}_2$), 4.2–4.55(1H,m,3-$\underline{H}$), 4.30(2H,q,J=7,—CO$_2$C$\underline{H}_2$CH$_3$), 3.03(1H,dd,J=9 & 18,4-$\underline{H}$), 2.75(1H,dd,J=6 & 18,4-$\underline{H}$), 1.29(3H,t,J=7,—CO$_2$CH$_2$C$\underline{H}_3$).

REFERENCE EXAMPLE 3

3-Amino-1-(2,2,2-trichloroethoxycarbonyl)succinimide hydrobromide

In 20 ml of carbon tetrachloride was suspended 20 g of 3-benzyloxycarbonylamino-1-(2,2,2-trichloroethoxycarbonyl)succinimide, followed by addition of 25 g of a 30% solution of hydrogen bromide in acetic acid. The mixture was stirred at room temperature for one hour and, following addition of 400 ml of ethyl ether, it was allowed to stand in a refrigerator to give crystals of 3-amino-1-(2,2,2-trichloroethoxycarbonyl)succinimide hydrobromide. Yield 16 g.

Elemental analysis: Calcd. for $C_7H_7N_2O_4Cl_3$·HBr: C, 22.69; H, 2.18; N, 7.56; Cl, 28.72; Br, 21.57. Found: C, 22.99; H, 2.24; N, 7.70; Cl, 28.54; Br, 21.67.

IR $\nu_{max}^{KBr}$ cm$^{-1}$: 1830, 1780, 1740

NMR(DMSO-d$_6$)δ: 8.74(3H,broad s, -N$\underline{H}_3^+$), 5.18(2H,s,—CO$_2$C$\underline{H}_2$CCl$_3$), 4.58(1H,dd,J=7 & 9, 3-$\underline{H}$), 3.21(1H,dd, J=9 & 18,4-$\underline{H}$), 2.91(1H,dd,J=7 & 18,4-$\underline{H}$).

REFERENCE EXAMPLE 4

3-Amino-1-ethoxycarbonylsuccinimide hydrobromide

In the same manner as Reference Example 3, 20 g of 1-ethoxycarbonyl-3-benzyloxycarbonylaminosuccinimide was treated with hydrobromic acid to remove the benzyloxycarbonyl group. The procedure gave 16.4 g of 3-amino-1-ethoxycarbonylsuccinimide hydrobromide as white powder.

Elemental analysis: Calcd. for $C_7H_{10}N_2O_4$·HBr: C, 31.48; H, 4.15; N, 10.49; Br, 29.92. Found: C, 31.69; H, 4.38; N, 10.18; Br, 30.19.

IR $\nu_{max}^{KBr}$ cm$^{-1}$: 1830, 1778, 1735.

NMR(DMSO-d$_6$)δ: 8.63(3H,broad s,-N$\underline{H}_3^+$), 4.37(2H,q,J=7, —CO$_2$C$\underline{H}_2$CH$_3$), 2.5–3.5(3H,m,3-$\underline{H}$ & 4-$\underline{H}$), 1.41 (3H,t,J=7,—CO$_2$CH$_2$C$\underline{H}_3$).

REFERENCE EXAMPLE 5

3-Bromo-1-(2,2,2-trichloroethoxycarbonyl)succinimide

In 170 ml of 10% sulfuric acid was dissolved in 30 g of potassium bromide, followed by addition of 150 ml of ethyl acetate. The mixture was cooled to $-15°$ to $-10°$ C. and 3-amino-1-(2,2,2-trichloroethoxycarbonyl)succinimide hydrobromide was suspended. While the mixture was stirred vigorously at the same temperature as above, 9.4 g of sodium nitrile was added. After the mixture was further stirred at 0°–5° C. for one hour, the ethyl acetate layer was separated and the aqueous layer was further extracted with ethyl acetate. These ethyl acetate extracts were combined, washed with water, dried over magnesium sulfate and concentrated under reduced pressure. The concentrate was chromatographed on a silica gel column pretreated with an oxalic acid-saturated mixuture of toluene and ethyl acetate (9:1) and eluted with the same solvent system. The eluate was washed with water, dried over magnesium sulfate and concentrated under reduced pressure. To the concentrate was added a 1:10 mixture of ethyl ether and petroleum ether, and finally the mixture was allowed to stand in a refrigerator, whereupon crystals separated out. Yield 3.5 g.

Elemental analysis: Calcd. for $C_7H_5NO_4BrCl_3$: C, 23.79; H, 1.43; N, 3.96 Cl, 30.10; Br, 22.61. Found: C, 23.98; H, 1.32; N, 3.99 Cl, 30.59; Br, 22.50.

IR $\nu_{max}^{KBr}$ cm$^{-1}$: 1830, 1755.

NMR(CDCl$_3$)δ: 4.97(2H,s,—CO$_2$C$\underline{H}_2$CCl$_3$), 4.74(1H,dd,J=4 & 8, 3-$\underline{H}$), 3.58(1H,dd,J=8 & 20,4-$\underline{H}$), 3.12(1H,dd, J=4 & 20,4-$\underline{H}$).

REFERENCE EXAMPLE 6

3-Bromo-1-ethoxycarbonylsuccinimide

In the same manner as Reference Example 5, 25.0 g of 3-amino-1-ethoxycarbonylsuccinimide hydrobromide was reacted with nitrosyl bromide to give 2.5 g of 3-bromo-1-ethoxycarbonylsuccinimide as an oil.

Elemental analysis: Calcd. for $C_7H_8NO_4Br$: C, 33.62; H, 3.22; N, 5.60; Br, 31.96. Found: C, 33.93; H, 3.15; N, 5.51; Br, 31.88.

IR $\nu_{max}^{KBr}$ cm$^{-1}$: 1818, 1770, 1735.

NMR(CDCl$_3$)δ: 4.62(1H,dd,J=3.5 & 8,3-$\underline{H}$), 4.41(2H,q,J=7, —CO$_2$C$\underline{H}_2$CH$_3$), 3.52(1H,dd,J=8 & 17,4-$\underline{H}$), 3.03 (1H,dd,J=3.5 & 17,4-$\underline{H}$), 1.38(3H,t,J=7, —CO$_2$CH$_2$C$\underline{H}_3$).

REFERENCE EXAMPLE 7

3-[Acetylamino-di(ethoxycarbonyl)methyl]-1-(2,2,2-trichloroethoxycarbonyl)succinimide In 25 ml of ethanol was dissolved 235 mg of sodium, and following addition of 2.3 g of diethyl acetamidomalonate, the mixture was refluxed for 2 hours. The reaction mixture was cooled to $-40°$ C., followed by addition of 3.3 g of 3-bromo-1-(2,2,2-trichloroethoxycarbonyl)succinimide. This mixture was stirred at $-5°$ to 0° C. for 30 minutes and, following addition of 1 ml of acetic acid, it was concentrated under reduced pressure. The residue was poured into a mixture of ethyl acetate and 10% aqueous sodium chloride. The mixture was stirred, after which the ethyl acetate layer was separated, washed with water, dried over magnesium sulfate and concentrated under reduced pressure. The concentrate was chromatographed on a silica gel column and the column was washed with toluene-ethyl acetate (4:1), elution being carried out with toluene-ethyl acetate (4:1). The eluate was concentrated under reduced pressure, followed by addition of ethyl acetate. The mixture was finally allowed to stand in a refrigerator, whereupon crystals separated out. Yield 0.7 g.

Elemental analysis: Calcd. for $C_{16}H_{19}N_2O_9Cl_3$: C, 39.24; H, 3.91; N, 5.72; Cl, 21.72. Found: C, 39.53; H, 3.88; N, 5.59; Cl, 22.15.

IR $\nu_{max}^{KBr}$ cm$^{-1}$: 1820, 1800, 1780, 1705.

NMR(CDCl$_3$)δ: 7.14(1H,s,—CON$\underline{H}$—), 5.20(2H,s,—C$\underline{H}_2$CCl$_3$), 4.36 (2H,q,J=7,—C$\underline{H}_2$CH$_3$), 4.20(2H,q,J=7,—C$\underline{H}_2$CH$_3$), 3.5–4.0(1H,m,3—H), 2.5–3.5(2H,m,4—$\underline{H}$x2), 1.95(3H,s,C$\underline{H}_3$CO—), 1.31(3H,t,J=7,—CH$_2$C$\underline{H}_3$), 1.19(3H,t,CH$_2$C$\underline{H}_3$).

REFERENCE EXAMPLE 8

3-[Acetylamino-di(ethoxycarbonyl)methyl]-2,5-dioxopyrrolidine

In 10 ml of dimethylformamide was dissolved 600 mg of 3-[acetylamino-di(ethoxycarbonyl)methyl]-1-(2,2,2-trichloroethoxycarbonyl)succinimide and following addition of 1 ml of acetic acid, the mixture was cooled to $-10°$ to $-15°$ C. Then, 0.5 g of zinc dust was added and the mixture was stirred at the same temperature as above for 2 hours. The reaction mixture was filtered and the insoluble materials were washed with 200 ml of chloroform. The filtrate and washings were combined, washed with 1 N hydrochloric acid and water, dried over magnesium sulfate and concentrated under reduced pressure. To the residue was added ethyl ether and the mixture was allowed to stand in a refrigerator overnight, whereupon crystals separated out. Yield 210 mg.

REFERENCE EXAMPLE 9

3-[Acetylamino-di(ethoxycarbonyl)methyl]-2,5-dioxopyrrolidine

In 1 l of ethanol was dissolved 31.6 g of sodium, and following addition of 300 g of diethyl acetylaminomalonate at room temperature, the mixture was stirred for 2 hours. To the reaction mixture, a solution of 144.5 g of methyl 2-bromosuccinamate in ethanol (350 ml) was added dropwise under ice-cooling and the mixture was stirred under ice-cooling for one hour and then at room temperature for an additional one hour. This reaction mixture was concentrated under reduced pressure, followed by addition of 1 l portions of water and ethyl acetate, and stirred. The aqueous layer was separated and the ethyl acetate layer was further extracted with 500 ml of water. These aqueous layers were combined, washed with 1 l of ethyl acetate, adjusted to pH 1.5 with conc. hydrochloric acid and allowed to stand in a refrigerator. The resultant crystals were collected by filtration, washed with water and dried under reduced pressure. Yield 140 g.

The crystallization mother liquor and washings were combined, concentrated to about 1 l and extracted four times with 250 ml portions of ethyl acetate. The ethyl acetate extract was washed with saturated aqueous sodium chloride, dried over sodium sulfate and concentrated under reduced pressure. To the residue was added 1 l of ethyl ether and the mixture was allowed to stand in a refrigerator. The resultant crystals were collected by filtration and washed with ethyl ether to give 11 g of crystals as a further crop.

Elemental analysis: Calcd. for $C_{13}H_{18}N_2O_7$: C, 49.68; H, 5.77; N, 8.91. Found: C, 49.67; H, 5.70; N, 8.85.

IR $\nu_{max}^{KBr}$ cm$^{-1}$: 1790, 1740, 1718, 1700.

NMR(DMSO-d$_6$)δ: 11.2(1H,broad s,—CON$\underline{H}$CO—), 8.29(1H,s, —CON$\underline{H}$—), 4.19(2H,q,J=6,—CO$_2$C$\underline{H}_2$CH$_3$), 4.08(2H,q,J=6,—CO$_2$C$\underline{H}_2$CH$_3$), 3.74(1H,t, J=7,3—$\underline{H}$), 2.82(2H,d,J=7,4—$\underline{H}$), 1.92(3H,s, —NHCOC$\underline{H}_3$), 1.21(3H,t,J=6,—CO$_2$CH$_2$C$\underline{H}_3$), 1.15(3H,t,J=6,—CO$_2$CH$_2$C$\underline{H}_3$).

REFERENCE EXAMPLE 10

3-[Acetylamino-di(ethoxycarbonyl)methyl]-2,5-dioxopyrrolidine

In 100 ml of ethanol was dissolved 3.4 g of sodium, and following addition of 32 g of diethyl acetylaminomalonate, the mixture was refluxed for 2 hours. To the reaction mixture was added dropwise a solution of 16.5 g of ethyl 2-bromosuccinamate in ethanol (40 ml) and under stirring the mixture was refluxed for 30 minutes. This reaction mixture was concentrated under reduced pressure, followed by addition of ethyl acetate and water, and stirred. The aqueous layer was separated and the ethyl acetate layer was extracted with water. These aqueous extracts were combined, washed with ethyl acetate, adjusted to pH 1.5 with conc. hydrochloric acid and extracted with ethyl acetate. The extract was washed with water, dried over anhydrous sodium sulfate and concentrated under reduced pressure. To the residue was added ethyl ether and the mixture was allowed to stand in a refrigerator, whereupon crystals separated out. Yield 7.3 g.

EXAMPLE 1

(2,5-Dioxopyrrolidin-3-yl)glycine

In 1.5 l of 2 N-hydrochloric acid was suspended 60 g of 3-[acetylamino-di(ethoxycarbonyl)methyl]-2,5-dioxopyrrolidine and the suspension was refluxed with stirring for 15 hours. The reaction mixture was concentrated to dryness under reduced pressure under azeotropic distillation with n-butanol and the residue was dissolved in 1 l of water. This solution was adjusted to pH 2–2.5 with a saturated aqueous solution of sodium hydrogen carbonate and allowed to stand in a refrigerator, whereupon crystals separated out. Yield 9.3 g. The crystallization mother liquor and washings were combined and adsorbed on a column (1 l) of Amberlite IRA-68 (OH$^-$-form, Rohm and Haas Co.). After the column was washed with water, elution was carried out with 3% acetic acid. The fractions containing the desired compound were pooled and concentrated under reduced pressure to give 2.1 g of crystals.

The mother liquor was subjected to column chromatography on activated carbon (250 ml) and eluted with water. The eluate was concentrated under reduced pressure to give 1.2 g of crystals as a further crop.

Elemental analysis: Calcd. for $C_6H_8N_2O_4$: C, 41.86; H, 4.68; N, 16.28. Found: C, 41.79; H, 4.51; N, 16.28.

IR $\nu_{max}^{KBr}$ cm$^{-1}$: 1738, 1715.

NMR(D$_2$O+DCl)δ: 4.87(1H,d,J=5,

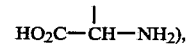

3.87(1H, ddd, J=5 & 5.5 & 9,3—$\underline{H}$), 3.28(1H,dd,J=9 & 18, 4—$\underline{H}$), 2.87(1H,dd,J=5.5 & 18,4—$\underline{H}$).

EXAMPLE 2

Benzyloxycarbonyl-2-(2,5-dioxopyrrolidin-3-yl)glycine

In 250 ml of water-dioxane (1:1) was suspended 10 g of 2-(2,5-dioxopyrrolidin-3-yl)glycine and under cooling at 0°–5° C. the above amino acid was dissolved by addition of 70 ml of 1 N sodium hydroxide. To this solution was added 15 ml of benzyloxycarbonyl chloride and, with adjusting pH to 7.1–7.4 with sodium hydrogen carbonate, the mixture was stirred at the same temperature as above for 2 hours. The reaction mixture was concentrated under reduced pressure to remove the organic solvent and the concentrate was washed with ethyl acetate. The aqueous layer was adjusted to pH 1 with conc. hydrochloric acid and allowed to stand in a refrigerator overnight to give crystals. Yield 15.8 g.

Elemental analysis: Calcd. for $C_{14}H_{14}N_2O_6$: C, 54.90; H, 4.61; N, 9.15. Found: C, 54.83; H, 4.72; N, 9.08.

IR $\nu_{max}^{KBr}$ cm$^{-1}$: 1785(sh), 1735, 1720.

NMR(DMSO-d$_6$)δ: 11.15(1H,s,—CON$\underline{H}$CO—), 7.74(1H,d,J=9,—CON$\underline{H}$—), 7.33(5H,s,C$_6$H$_5$—), 5.00(2H,s,C$_6$H$_5$C$\underline{H}_2$—), 4.62(1H,dd,J=4 & 9,

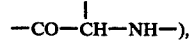

3.25–3.55 (1H,m,3—H), 2.3–2.9(2H,m,4—Hx2).

EXAMPLE 3

Benzyloxycarbonyl-2-(2,5-dioxopyrrolidin-3-yl)glycine methyl ester

In 300 ml of methanol was dissolved 2 g of benzyloxycarbonyl-2-(2,5-dioxopyrrolidin-3-yl)glycine and under ice-cooling an excess of an ethereal solution of diazomethane was added. The mixture was stirred under ice-cooling for 2 hours and then concentrated under reduced pressure. The concentrate was chromatographed on a silica gel column and eluted with toluene-acetone (4:1). The eluate was concentrated under reduced pressure and after addition of ethyl ether to the residue, the mixture was allowed to stand in a refrigerator overnight to give crystals. Yield 1.3 g.

Elemental analysis: Calcd. for $C_{15}H_{16}N_2O_6$: C, 56.25; H, 5.04; N, 8.75. Found: C, 56.01; H, 5.12; N, 8.67.

IR $\nu_{max}^{KBr}$ cm$^{-1}$: 1795, 1740, 1693.

NMR(DMSO-d$_6$)δ: 11.23(1H,br.s,—CONHCO—), 7.98(1H,d,J=9, —CONH—), 7.39(5H,s,C$_6$H$_5$CH$_2$—), 5.08(2H,s, C$_6$H$_5$CH$_2$—), 4.68(1H,dd,J=4.5 & 9,

3.63(3H,s,—CO$_2$CH$_3$), 3.1–3.5(1H,m,3—H), 2.2–2.95(2H,m,4—Hx2).

EXAMPLE 4

Benzyloxycarbonyl-2-(2,5-dioxopyrrolidin-3-yl)glycine methyl ester

In 300 ml of methanol was suspended 10 g of benzyloxycarbonyl-2-(2,5-dioxopyrrolidin-3-yl)glycine and, under cooling at −20° C. or below, 10 g of thionyl chloride was added dropwise. The mixture was stirred at 0°–5° C. for 4 hours and then at room temperature for 20 hours. The reaction mixture was concentrated under reduced pressure and the residue was dissolved in ethyl acetate. The ethyl acetate solution was washed with water, dried over sodium sulfate and concentrated under reduced pressure. The concentrate was chromatographed on a silica gel column and eluted with toluene-acetone (4:1). The eluate was concentrated under reduced pressure and to the residue was added ethyl ether to give crystals. Yield 5.8 g.

EXAMPLE 5

Benzyloxycarbonyl-2-[1-(2,4-dimethoxybenzyl)-2,5-dioxopyrrolidin-3-yl]glycine methyl ester In 100 ml of tetrahydrofuran were dissolved 3.2 g of benzyloxycarbonyl-2-(2,5-dioxopyrrolidin-3-yl)glycine methyl ester, 1.8 g of 2,4-dimethoxybenzyl alcohol and 3.9 g of triphenylphosphine and under ice-cooling 2 ml of diethyl azodicarboxylate was added. The mixture was stirred at room temperature for one hour and concentrated under reduced pressure. The residue was dissolved in ethyl acetate, and the solution was washed with 5% sodium hydrogen carbonate and 10% phosphoric acid in that order and dried over sodium sulfate. The solution was concentrated under reduced pressure and the concentrate was chromatographed on a silica gel column, elution being carried out with toluene-ethyl acetate (7:3). The eluate was concentrated under reduced pressure and the residue was added petroleum ether. The precipitate was collected by filtration and dried. Yield 1.2 g IR $\nu_{max}^{KBr}$ cm$^{-1}$: 1785(sh), 1725, 1705.

EXAMPLE 6

2-[1-(2,4-Dimethoxybenzyl)-2,5-dioxopyrrolidin-3-yl]glycine methyl ester

In a mixture of 50 ml of methanol and 5 ml of acetic acid was dissolved 3 g of benzyloxycarbonyl-2-[1-(2,4-dimethoxybenzyl)-2,5-dioxopyrrolidin-3-yl]glycine methyl ester and after addition of 500 mg of palladium black, the mixture was stirred in a stream of hydrogen at room temperature for 2.5 hours. The catalyst was filtered off and the filtrate was concentrated to dryness under reduced pressure. The concentrate was chromatographed on a silica gel column and eluted with toluene-acetone (4:1). The eluate was concentrated under reduced pressure and to the residue was added 100 ml of ethyl ether-petroleum ether (1:5). The mixture was allowed to stand in a refrigerator overnight and the resulting precipitate was collected by filtration and dried. Yield 1.4 g.

EXAMPLE 7

Benzyloxycarbonyl-2-(2,5-dioxopyrrolidin-3-yl)glycine 2,2,2-trichloroethyl ester In 50 ml of tetrahydrofuran was dissolved 6.2 g of benzyloxycarbonyl-2-(2,5-dioxopyrrolidin-3-yl)glycine and, following addition of 1.2 ml of pyridine, a solution of 5.4 g of 2,2,2-trichloroethyl chloroformate in 30 ml of tetrahydrofuran was added dropwise under cooling at 0°–5° C. The reaction mixture was stirred at the same temperature as above for 30 minutes and under reflux for 5 minutes and then concentrated to dryness under reduced pressure. The residue was extracted with ethyl acetate and the extract was washed with water, dried over sodium sulfate and concentrated under reduced pressure. The concentrate was chromatographed on a silica gel column and eluted with toluene-ethyl acetate (3:1). The eluate was concentrated under reduced pressure, and the residue was dissolved in a small amount of ethyl ether. After addition of petroleum ether to the solution, the mixture was allowed to stand in a refrigerator overnight to give crystals. Yield 1.1 g.

Elemental analysis: Calcd. for $C_{16}H_{15}N_2O_6Cl_3$: C, 43.90; H, 3.46; N, 6.40; Cl, 24.30. Found: C, 43.85; H, 3.17; N, 6.39; Cl, 24.59.

IR $\nu_{max}^{KBr}$ cm$^{-1}$: 1775, 1730, 1715.

NMR(DMSO-d$_6$)δ: 11.01(1H,broad s,—CONH-CO—), 7.37(5H,s, C$_6$H$_5$—), 7.05(1H,d,J=9,—CONH—), 5.13(2H,s, —OCH$_2$—), 4.91(1H,dd,J=4.5 & 9

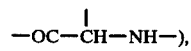

4.81(2H,s,—OCH$_2$—), 3.35–3.65(1H,m,3—H), 2.5–3.1(2H,m,4—H).

EXAMPLE 8

Benzyloxycarbonyl-2-(2,5-dioxopyrrolidine-3-yl)glycine 2,2,2-trichloroethyl ester In 30 ml of tetrahydrofuran were dissolved 1.53 g of benzyloxycarbonyl-2-(2,5-dioxopyrrolidin-3-yl)glycine and 1 ml of 2,2,2-trichloroethanol and under cooling at 0°–5° C., 0.8 ml of pyridine was added. Then, 1.2 g of dicyclohexylcarbodiimide was added and the mixture was stirred at the same temperature as above for 2 hours and at room temperature for 18 hours. The precipitated dicyclohexylurea separating out was filtered off and the filtrate was concentrated under reduced pressure. The residue was added to a mixture of 2 N hydrochloric acid and ethyl acetates and the ethyl acetate layer was separated, washed with 2 N hydrochloric acid, dried over sodium sulfate and concentrated under reduced pressure. The concentrate was chromatographed on a silica gel column and eluted with toluene-ethyl acetate (3:1). The eluate was concentrated under reduced pressure and the residue was crystallized from ethyl ether-petroleum ether. Yield 0.7 g.

EXAMPLE 9

Benzyloxycarbonyl-2-(2,5-dioxopyrrolidin-3-yl)glycine benzyl ester

In 100 ml of tetrahydrofuran were dissolved 4.6 g of benzyloxycarbonyl-2-(2,5-dioxopyrrolidin-3-yl)glycine and 2.5 ml of benzyl alcohol, and under cooling at 0°–5° C. 2.4 ml of pyridine and 3.6 g of dicyclohexylcarbodiimide were added to the solution in that order. The mixture was stirred at the same temperature as above for 4 hours and then at room temperature for 18 hours. The precipitated dicyclohexylurea were filtered off and the filtrate was concentrated under reduced pressure. The residue was poured into a mixture of 300 ml of 2 N hydrochloric acid and 300 ml of ethyl acetate. The ethyl acetate layer was separated, washed with 2 N hydrochloric acid, dried over sodium sulfate and concentrated under reduced pressure. The concentrate was chromatographed on a silica gel column and eluted with toluene-ethyl acetate (3:1). The eluate was concentrated under reduced pressure and the residue was dissolved in a small amount of ethyl ether. To this solution was added petroleum ether to give crystals. Yield 4.8 g.

Elemental analysis: Calcd. for $C_{21}H_{20}N_2O_6$: C, 63.63; H, 5.09; N, 7.07. Found: C, 63.48; H, 5.31; N, 7.47.

IR $\nu_{max}^{KBr}$ cm$^{-1}$: 1780(sh), 1720, 1700

NMR(DMSO-d$_6$)δ: 11.21(1H,broad s,—CON$\underline{H}$—CO—), 8.02(1H,d, J=9,—CON$\underline{H}$—), 7.37(10H,s,C$_6$H$_5$—), 5.13(2H, s,—OC$\underline{H}_2$—), 5.07(2H,s,—OC$\underline{H}_2$—), 4.72(1H,dd, J=4.5 & 9

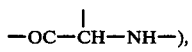

3.2–3.45(1H,m, 3—$\underline{H}$), 2.2–2.9(2H,m,4—$\underline{H}$).

EXAMPLE 10

Benzyloxycarbonyl-L-alanyl-2-(2,5-dioxopyrrolidin-3-yl)glycine sodium salt

In 40 ml of tetrahydrofuran was dissolved 2.2 g of benzyloxycarbonyl-L-alanine and under cooling at −30° C., 2 g of phosphorus pentachloride was added. The mixture was stirred at −20° to −15° C. for 30 minutes. In 50 ml of a 20% solution of methanol in water was suspended 1.4 g of 2-(2,5-dioxopyrrolidin-3-yl)glycine and the suspension was adjusted to pH 8–9 with triethylamine and cooled to −15° to −10° C. To this suspension was added dropwise the previously prepared mixture and, with adjusting its pH to 8–9 with triethylamine, the mixture was stirred at −10° to −5° C. for one hour and then at room temperature for 30 minutes. This reaction mixture was adjusted to pH 7 with 2 N hydrochloric acid and concentrated under reduced pressure. To the residue were added water and ethyl acetate and the mixture was stirred. The aqueous layer was separated and the ethyl acetate layer was further extracted with water. These aqueous layers were combined, adjusted to pH 2 or below with conc. hydrochloric acid, saturated with sodium chloride, and extracted with ethyl acetate. The ethyl acetate extract was washed with saturated aqueous sodium chloride and following addition of water it was adjusted to pH 5 with a 5% solution of sodium hydrogen carbonate under stirring. The aqueous layer was separated and the ethyl acetate layer was further extracted with water. These aqueous layers were combined and concentrated under reduced pressure. The concentrate was chromatographed on a column (250 ml) of MCI gel CHP 20P (Mitsubishi Chemical Industries, Ltd. Japan) and after the column was washed with water, gradient elution was carried out with water and aqueous methanol (up to the methanol concentration of 40%). The eluate was concentrated under reduced pressure and lyophilized to give benzyloxycarbonyl-L-alanyl-2-(2,5-dioxopyrrolidin-3-yl)glycine sodium salt.

Elemental analysis: Calcd. for $C_{17}H_{18}N_3O_7Na \cdot H_2O$: C, 48.92; H, 4.83; N, 10.07. Found: C, 48.83; H, 5.05; N, 10.14.

IR $\nu_{max}^{KBr}$ cm$^{-1}$: 1780, 1725, 1710, 1620

NMR(D$_2$O)δ: 7.49(5H,s,—C$\underline{H}_2$C$_6$H$_5$), 5.21(2H,s,—C$\underline{H}_2$C$_6$H$_5$), 4.72(1H,d,J=5

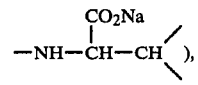

4.23(1H,q,J=7,

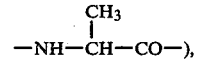

3.2–3.6(1H,m,3—$\underline{H}$), 2.2–3(2H,m, 4—$\underline{H}$), 1.46(3H,d,J=7,>CHC$\underline{H}_3$).

EXAMPLE 11

Benzyloxycarbonyl-L-alanyl-2-(2,5-dioxopyrrolidin-3-yl)glycine benzhydryl ester In the same manner as Example 10, 7.5 g of (2,5-dioxopyrrolidin-3-yl)glycine was acylated with benzyloxycarbonyl-L-alanyl chloride to give benzyloxycarbonyl-L-alanyl-2-(2,5-dioxopyrrolidin-3-yl)glycine. To a solution of the above dipeptide derivative in ethyl acetate was added diphenyldiazomethane until reddish purple color stayed, and the mixture was stirred at room temperature for one hour. The reaction mixture was washed with water, dried over sodium sulfate and concentrated under reduced pressure. The concentrate was chromatographed on a silica gel column and eluted with toluene-ethyl acetate (1:1). The eluate was concentrated under reduced pressure and a mixture of ethyl ether and petroleum (1:4) was added to the residue. The mixture was allowed to stand in a refrigerator, whereupon benzhydryl ester precipitates. Yield 16 g.

Elemental analysis: Calcd. for $C_{29}H_{29}N_3O_7$: C, 65.52; H, 5.50; N, 7.91. Found: C, 65.42; H, 5.64; N, 7.81.

IR $\nu_{max}^{KBr}$ cm$^{-1}$: 1780(sh), 1740, 1700.

NMR(DMSO-d$_6$)δ: 7.35(15H,s,C$_6$H$_5$x3), 6.77(1H,s,—C$\underline{\text{H}}$(C$_6$H$_5$)$_2$), 4.98(2H,s,C$_6$H$_5$—C$\underline{\text{H}}_2$—), 4.85–5.1(1H,m,

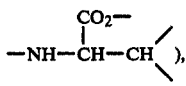

3.9–4.3(1H,m,

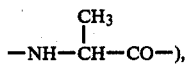

3.3–3.6(1H,m,3—$\underline{\text{H}}$), 2.3–2.7(2H,m,4—$\underline{\text{H}}$), 1.05–1.25(3H,m

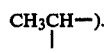

EXAMPLE 12

Benzyloxycarbonyl-D-alanyl-2-(2,5-dioxopyrrolidin-3-yl)glycine

In 60 ml of tetrahydrofuran was dissolved 5.2 g of benzyloxycarbonyl-D-alanine and, following addition of 5 g of phosphorus pentachloride under cooling at −30° C., the mixture was stirred at <20° to −15° C. for 30 minutes. On the other hand, 1.7 g of 2-(2,5-dioxopyrrolidin-3-yl)glycine was suspended in 150 ml of water-methanol (2:1) and, after the suspension was cooled to −10°∼ −15° C., it was adjusted to pH 10.5 with triethylamine for dissolution. To this solution were added 5 ml portions of the above-mentioned solution of benzyloxycarbonyl-D-alanyl chloride. The mixture was adjusted to pH 10–10.5 with triethylamine and stirred at −15° to −10° C. for one hour. It was adjusted again to pH 9.5 and stirred at 0°–5° C. for an additional one hour. The reaction mixture was adjusted to pH 5 with 2 N hydrochloric acid and concentrated under reduced pressure. The concentrate was adjusted to pH 1 with conc. hydrochloric acid and extracted four times with ethyl acetate. The ethyl acetate extracts were combined and washed with saturated aqueous sodium chloride. Water was added to the ethyl layer and adjusted to pH 5 by addition of water and dropwise addition of a saturated aqueous solution of sodium hydrogen carbonate under stirring. After the solution was stirred, the aqueous layer was separated and the ethyl acetate layer was extracted further with water. These extracts were combined, washed with ethyl acetate and concentrated under reduced pressure. The concentrate was chromatographed on a column (250 ml) of MIC gel CHP 20P and, after the column was washed with water, water to 40% methanol-water gradient elution was carried out. The eluate was concentrated under reduced pressure and lyophilized to give benzyloxycarbonyl-D-alanyl-2-(2,5-dioxopyrrolidin-3-yl)glycine sodium salt. Yield 1.3 g.

Elemental analysis: Calcd. for $C_{17}H_{18}N_3O_7Na\cdot 1.5\text{-}H_2O$: C, 47.89; H, 4.96; N, 9.86. Found: C, 47.91; H, 5.04; N, 9.77.

IR $\nu_{max}^{KBr}$ cm$^{-1}$: 1780, 1725, 1710, 1620.

EXAMPLE 13

L-Alanyl-2-(2,5-dioxopyrrolidin-3-yl)glycine hydrobromide

To 5.3 g of benzyloxycarbonyl-L-alanyl-2-(2,5-dioxopyrrolidin-3-yl)glycine benzhydryl ester was added 10 ml of a 30% solution of hydrogen bromide in acetic acid and the mixture was stirred at room temperature for one hour. To the reaction mixture was added ethyl ether and the resulting precipitate was collected by filtration. Yield 3.2 g.

Elemental analysis: Calcd. for $C_9H_{13}N_3O_5\cdot\text{HBr}$: C, 33.35; H, 4.35; N, 12.96. Found: C, 33.71; H, 4.18; N, 13.11.

IR $\nu_{max}^{KBr}$ cm$^{-1}$: 1780, 1730, 1695.

NMR(D$_2$O)δ: 4.78(1H,d,J=5

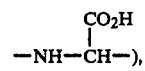

4.46(1H,q,J=7

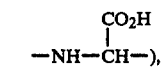

3.25–3.7(1H,m,3—$\underline{\text{H}}$), 2.2–2.95(2H,m,4—$\underline{\text{H}}$), 1.45 (3H,d,J=7

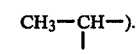

EXAMPLE 14

L-Alanyl-2-(2,5-dioxopyrrolidin-3-yl)glycine

In 20 ml of dimethylformamide were dissolved 1 g of 2-[1-(2,4-dimethoxybenzyl)-2,5-dioxopyrrolidin-3-yl]glycine methyl ester and 1.5 g of N-hydroxysuccinimide ester of benzyloxycarbonyl-L-alanine, and the solution was stirred at room temperature for 50 hours. The reaction mixture was concentrated under reduced pressure and the residue was dissolved in ethyl acetate, washed with 2 N hydrochloric acid and saturated sodium hydrogen carbonate, and dried over sodium sulfate and concentrated under reduced pressure. To the residue was added petroleum ether to give benzyloxycarbonyl-L-alanyl-2-[1-(2,4-dimethoxybenzyl)-2,5-dioxopyrrolidin-3-yl]glycine methyl ester as a white powder. This powder was dissolved in a mixture of 50 ml of methanol and 10 ml of acetic acid and stirred with 500 ml of palladium black in a stream of hydrogen at room temperature for 3 hours. The catalyst was filtered off and the filtrate was concentrated under reduced pressure. The residue was dried in a desiccator overnight and dissolved in 50 ml of methanol. With adjusting pH to 9–10 with 1 N sodium hydroxide, the solution was stirred at room temperature for 3 hours. This reaction mixture was adjusted to pH 5 and concentrated under reduced pressure. The residue was dried in a desiccator overnight, dissolved in 10 ml of a 30% solution of hydrogen bromide in acetic acid, and stirred at room temperature for 3 hours. The reaction mixture was concentrated under reduced pressure and the residue was dissolved in water and adjusted to pH 4 with saturated sodium hydrogen carbonate. It was chromatographed on a column (200 ml) of MCI gel CHP-20P, and water to 50% aqueous methanol-water gradient elution was carried out. The eluate was concentrated under reduced pressure and lyophilized to give L-alanyl-2-(2,5-dioxopyrrolidin-3-yl)glycine as a white powder.

EXAMPLE 15

L-Alanyl-2-(5-hydroxy-2-oxopyrrolidin-3-yl)glycine

In 20 ml of water was dissolved 3.2 g of L-alanyl-2-(2,5-dioxopyrrolidin-3-yl)glycine hydrobromide and the solution was adjusted to pH 6 with a saturated aqueous solution of sodium hydrogen carbonate and cooled to 0°–5° C. To this solution was added 1.5 g of sodium borohydride all at once. The mixture was stirred at the same temperature for one hour, while kept maintaining at pH 8.9–9.2 with 2 N hydrochloric acid. The reaction mixture was adjusted to pH 4.0 with 2 N hydrochloric acid, diluted with 200 ml of water and adsorbed on a column (150 ml) of Amberlite IRA-68 (OH$^-$-form). After the column was washed with water, elution was carried out with 0.2 N acetic acid. The eluate was concentrated to dryness under reduced pressure and the resultant powder was subjected to column chromatography on activated carbon and eluted with water. The eluate was concentrated under reduced pressure and lyophilized to give L-alanyl-2-(5-hydroxy-2-oxopyrrolidin-3-yl)glycine as a white powder.

Elemental analysis: Calcd. for C$_9$H$_{15}$N$_3$O$_9$.2H$_2$O: C, 38.42; H, 6.81; N, 14.94. Found: C, 38.18, H, 6.53; N, 15.19.

IR $\nu_{max}^{KBr}$ cm$^{-1}$: 1690, 1610.

NMR(D$_2$O)δ: 5.25–5.6(1H,m,5—H), 4.70(1H,d,J=5.5

—NHCH—CO$_2$H), 4.25(1H,q,J=7

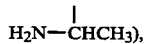
H$_2$N—CHCH$_3$), 2.1–3.6 & 1.6–1.9(3H, m,3—H & 4—H), 1.70(3H,d,J=7

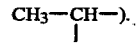
CH$_3$—CH—).

EXAMPLE 16

D-Alanyl-2-(5-hydroxy-2-oxopyrrolidin-3-yl)glycine

In 100 ml of water-methanol-acetic acid (1:1:0.2) was dissolved 2.0 g of benzyloxycarbonyl-D-alanyl-2-(2,5-dioxopyrrolidin-3-yl)glycine, and the solution was stirred with 600 mg of palladium black in a stream of hydrogen at room temperature for 2 hours. The reaction mixture was filtered and the filtrate was concentrated to dryness under reduced pressure. The residue was dissolved in 70 ml of water and, following addition of 580 mg of sodium borohydride at 0°–5° C., the mixture was stirred for 30 minutes with adjusting pH to 8.5–9.2 with 2 N hydrochloric acid. This reaction mixture was adsorbed on a column (150 ml) of Amberlite IRA-68 (OH$^-$-form) and after the column was washed with water, elution was carried out with 0.3 N acetic acid. The eluate was concentrated to dryness under reduced pressure and the resultant powder was subjected to column chromatography on activated carbon (250 ml) and eluted with water. The eluate was concentrated under reduced pressure and lyophilized to give D-alanyl-2-(5-hydroxy-2-oxopyrrolidin-3-yl)glycine as a white powder.

Elemental analysis: Calcd. for C$_9$H$_{15}$N$_3$O$_5$.2H$_2$O: C, 38.42; H, 6.81; N, 14.94. Found: C, 38.51; H, 6.43; N, 14.74.

IR $\nu_{max}^{KBr}$ cm$^{-1}$: 1685, 1610.

What we claim is:

1. A compound of the formula:

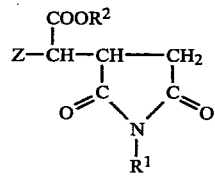

wherein Z is amino or amino protected by benzyloxycarbonyl, p-methoxybenzyloxycarbonyl, p-nitrobenzyloxycarbonyl, p-chlorobenzyloxycarbony, p-bromobenzyloxycarbonyl, tert-butoxycarbonyl or 2,2,2-trichloroethoxy-carbonyl; R$^1$ is hydrogen or 2,4-dimethoxybenzyl; and R$^2$ is hydrogen, methyl, ethyl, tert-butyl, 2,2,2-trichloroethyl, benzyl, p-methoxybenzyl, p-nitrobenzyl, trityl, benzhydryl, bis(p-methoxyphenyl)methyl or phenacyl.

* * * * *